United States Patent
Bodner et al.

(10) Patent No.: US 7,983,764 B2
(45) Date of Patent: Jul. 19, 2011

(54) CO-RADIAL LEAD WITH EXTENDABLE/RETRACTABLE FIXATION MECHANISM AND APPARATUS THEREFOR

(75) Inventors: Jeffrey P. Bodner, St. Paul, MN (US); Walter C. Laroche, Crystal, MN (US); Christopher P. Knapp, Ham Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1398 days.

(21) Appl. No.: 11/202,459

(22) Filed: Aug. 12, 2005

(65) Prior Publication Data

US 2007/0038280 A1 Feb. 15, 2007

(51) Int. Cl.
*A61N 1/00* (2006.01)

(52) U.S. Cl. ........ 607/116; 607/115; 607/119; 607/122; 607/126

(58) Field of Classification Search .................. 607/122, 607/126, 119
See application file for complete search history.

(56) References Cited

U.S. PATENT DOCUMENTS

| | | | |
|---|---|---|---|
| 4,646,755 A * | 3/1987 | Kane | 607/126 |
| 5,003,992 A * | 4/1991 | Holleman et al. | 607/120 |
| 5,129,404 A | 7/1992 | Spehr et al. | |
| 5,300,108 A * | 4/1994 | Rebell et al. | 607/127 |
| 5,683,446 A * | 11/1997 | Gates | 607/126 |
| 5,716,390 A * | 2/1998 | Li | 607/127 |
| 5,716,391 A * | 2/1998 | Grandjean | 607/127 |
| 5,752,915 A * | 5/1998 | Neubauer et al. | 600/373 |
| 5,769,858 A | 6/1998 | Pearson et al. | |
| 5,851,226 A * | 12/1998 | Skubitz et al. | 607/126 |
| 6,052,625 A * | 4/2000 | Marshall | 607/122 |
| 6,108,582 A | 8/2000 | Fischer | |
| 6,141,594 A * | 10/2000 | Flynn et al. | 607/127 |
| 6,321,102 B1 | 11/2001 | Spehr et al. | |
| 6,324,415 B1 | 11/2001 | Spehr et al. | |
| 6,379,351 B1 * | 4/2002 | Thapliyal et al. | 606/41 |
| 6,459,937 B1 * | 10/2002 | Morgan et al. | 607/126 |
| 6,463,334 B1 * | 10/2002 | Flynn et al. | 607/127 |
| 6,512,959 B1 * | 1/2003 | Gomperz et al. | 607/122 |
| 6,650,921 B2 | 11/2003 | Spehr et al. | |
| 6,687,550 B1 * | 2/2004 | Doan | 607/127 |
| 6,697,676 B2 * | 2/2004 | Dahl et al. | 607/126 |
| 6,763,270 B1 * | 7/2004 | Gomperz et al. | 607/126 |

(Continued)

FOREIGN PATENT DOCUMENTS

EP 0709111 A2 5/1996

(Continued)

*Primary Examiner* — Niketa I Patel
*Assistant Examiner* — Nicole F Lavert
(74) *Attorney, Agent, or Firm* — Faegre & Benson LLP

(57) ABSTRACT

A lead assembly comprises a lead body extending from a lead proximal end portion to a lead distal end portion with at least one conductor disposed therein. A lead lumen extends within the lead body and is dimensioned and configured to removably and rotatably seat a driver therein. The driver includes a driver body extending from a driver proximal end to a driver distal end and having a stylet or guidewire lumen disposed therein. An extendable and retractable active fixation mechanism is disposed at the lead distal end portion. The active fixation mechanism is actuatable by rotation of the driver. In one example, the at least one conductor includes a first conductor and a second conductor, in which the first conductor is co-radial with the second conductor. In another example, the driver distal end includes a portion extractably engagable with the lead distal end portion.

18 Claims, 14 Drawing Sheets

U.S. PATENT DOCUMENTS

| | | | |
|---|---|---|---|
| 6,792,317 B1 * | 9/2004 | Doan et al. | 607/122 |
| 6,819,959 B1 * | 11/2004 | Doan et al. | 607/127 |
| 6,968,237 B2 * | 11/2005 | Doan et al. | 607/122 |
| 7,184,842 B2 * | 2/2007 | Seifert et al. | 607/126 |
| 7,187,982 B2 * | 3/2007 | Seifert et al. | 607/126 |
| 2002/0035319 A1 | 3/2002 | Spehr et al. | |
| 2003/0167082 A1 * | 9/2003 | Ollivier et al. | 607/126 |
| 2003/0204233 A1 * | 10/2003 | Laske et al. | 607/127 |
| 2003/0220677 A1 * | 11/2003 | Doan et al. | 607/122 |
| 2004/0116939 A1 * | 6/2004 | Goode | 606/108 |
| 2004/0127967 A1 * | 7/2004 | Osypka | 607/122 |
| 2005/0065588 A1 * | 3/2005 | Zhao et al. | 607/125 |
| 2005/0065589 A1 * | 3/2005 | Schneider et al. | 607/126 |
| 2005/0070988 A1 * | 3/2005 | Kawula et al. | 607/126 |
| 2005/0080471 A1 * | 4/2005 | Chitre et al. | 607/122 |
| 2005/0137672 A1 * | 6/2005 | Coe et al. | 607/126 |
| 2005/0171588 A1 * | 8/2005 | Wahlstrom et al. | 607/126 |
| 2005/0177220 A1 * | 8/2005 | Iaizzo et al. | 607/126 |
| 2005/0182472 A1 * | 8/2005 | Wahlstrom et al. | 607/126 |
| 2005/0251240 A1 * | 11/2005 | Doan | 607/127 |
| 2006/0184221 A1 * | 8/2006 | Stewart et al. | 607/126 |
| 2006/0195091 A1 * | 8/2006 | McGraw et al. | 606/61 |
| 2006/0229693 A1 * | 10/2006 | Bauer et al. | 607/116 |
| 2006/0241737 A1 * | 10/2006 | Tockman et al. | 607/126 |
| 2007/0050005 A1 * | 3/2007 | Lauro | 607/126 |
| 2007/0100411 A1 * | 5/2007 | Bonde | 607/126 |
| 2007/0213798 A1 * | 9/2007 | Dreier et al. | 607/126 |

FOREIGN PATENT DOCUMENTS

| | | | |
|---|---|---|---|
| JP | 06125992 A | * | 5/1994 |
| JP | 10071208 A | * | 3/1998 |

* cited by examiner

CO-RADIAL LEAD WITH EXTENDABLE/RETRACTABLE FIXATION MECHANISM AND APPARATUS THEREFOR

TECHNICAL FIELD

This patent document pertains generally to cardiac leads. More particularly, but not by way of limitation, this patent document pertains to a co-radial lead with an extendable/retractable fixation mechanism and apparatus therefore.

BACKGROUND

Implantable leads represent the electrical link between an implantable medical device (often referred to simply as "IMD") and a subject's cardiac or other tissue, which is to be excited or sensed. An implantable lead may include a single or multiple conductors that are connected to an electrode or an electrode assembly at a lead intermediate portion or a lead distal end portion. A connector is included at a lead proximal end portion to form an electrical connection between the electrode or electrode assembly and the IMD.

To implant a lead within the subject, the lead is often fed intravenously toward the subject's heart. On its way to the heart, the lead may be required to travel through vasculature having increasingly smaller diameters. Like any foreign body introduced into the vasculature system, the lead may present an obstruction to the normal flow of blood. The magnitude of blood flow area of a given vessel obstructed by the lead is, in part, a function of the diameter of the lead body. Once the lead is implanted within the subject and the electrode or electrode assembly is positioned at a desired location within, on, or about the subject's heart, it is often desirable to provide some active method and apparatus for securing the electrode or electrode assembly at such location.

After a lead has been implanted and secured as desired by an implanting physician, the lead may occasionally fail. Upon failure of an implantable lead, it may in some cases, as for example in pacemaker-dependent or defibrillator-dependent subjects, become necessary to implant a replacement lead. Replacement leads may also be required in situations where it is desired to stimulate or shock a different cardiac site than that stimulated or shocked with an existing lead. One potential issue of removing inoperative implanted leads relates to the application of a pulling force upon the lead proximal end. For example, the flexible sheath of leads that have been implanted within a subject for long periods of time may deteriorate over time as a result of exposure to the harsh in vivo environment.

Accordingly, there is a need for a lead having a lead body with a reduced size (i.e., outer diameter). In addition, there is a need for a lead having an intermediate portion or a lead distal end portion that may actively be secured at a desired location within, on, or about a subject's heart. Furthermore, there is a need for a method and apparatus for the extraction of inoperative leads.

SUMMARY

A lead assembly comprises a lead body extending from a lead proximal end portion to a lead distal end portion with at least one conductor disposed therein. An extendable and retractable active fixation mechanism is disposed at the lead distal end portion. A lead lumen extends within the lead body from the lead proximal end portion to at least an active fixation mechanism proximal end and is dimensioned and configured to seat a removable and rotatable driver therein. The driver is dimensioned and configured to actuate the active fixation mechanism when rotated and includes a stylet or guidewire receiving lumen therein.

Several options for the lead assembly are as follows. In one example, the at least one conductor includes a first conductor and a second conductor, in which the first conductor is co-radial with the second conductor. In another example, the lead lumen is formed, at least in part, by the at least one conductor. In yet another example, a driver distal end includes a portion detachably matable with the active fixation mechanism proximal end. In a further example, the driver distal end includes a portion extractably engagable with the lead distal end portion, such as via the active fixation mechanism.

Other options are as follows. In one example, a driver proximal end includes a portion couplable with a rotation facilitating tool. In another example, the driver is composed, at least in part, of one or a combination of polyethylene terephthalate (referred to as "PET"), polyimide, polyethylene tetrafluoroethylene (referred to as "ETFE"), polytetrafluoroethylene (referred to as "PTFE"), or polyurethane. In yet another example, the driver is composed, at least in part, of a coil or a braided metal wire.

A method of manufacturing a lead assembly includes forming a lead body extending from a lead proximal end portion to a lead distal end portion and including a lead lumen formed therein. The method includes disposing an extendable and retractable active fixation mechanism at the lead distal end portion. The method further includes forming a longitudinally extending removable and rotatable driver including a stylet or guidewire receiving lumen therein and a driver distal end portion detachably matable with a proximal end of the active fixation mechanism.

Several options for manufacturing a lead assembly are as follows. In one example, the method includes inserting the driver within the lead lumen. In another example, forming the lead lumen includes positioning two or more co-radial conductors within the lead body. In yet another example, forming the driver includes forming a driver proximal end portion couplable with a rotation facilitating tool. Other options are as follows. In one example, the method further comprises inserting a stylet into the stylet or guidewire receiving lumen. In another example, forming the driver includes forming the driver distal end to extractably engage with the lead distal end portion.

A method of installing a lead includes introducing a lead assembly into a subject, in which the lead assembly includes a lead body having a lead proximal end portion, a lead distal end portion, and a lead lumen therein. The lead assembly further includes a driver, including a stylet or guidewire receiving lumen, removably and rotatably seated within the lead lumen. The method further includes extending or retracting an active fixation mechanism disposed at the lead distal end portion by way of detachable engagement of a driver distal end with an active fixation mechanism proximal end. Further yet, the method includes removing the driver from the lead lumen.

Several options for installing a lead are as follows. In one example, extending or retracting the active fixation mechanism includes selectively rotating a driver proximal end in a first (e.g., clockwise) or a second (e.g., counterclockwise) direction. In one such example, rotating the driver proximal end in the first direction affects extension of the active fixation mechanism from the lead body. hi another such example, rotating the driver proximal end in the second direction affects retraction of the active fixation mechanism within the lead body. In yet another example, rotating the driver proximal end includes coupling a rotation facilitating tool to the driver proximal end. Other options are as follows. In one example, the method further comprises inserting a stylet into the stylet or guidewire receiving lumen. In another example, the method further comprises removing the stylet from the stylet or guidewire receiving lumen.

A method of extracting a lead from a subject includes introducing a driver into a lead lumen, in which the driver includes a driver body having a driver proximal end, a driver distal end, and a stylet or guidewire receiving lumen therein. The driver further includes a stylet disposed within the stylet or guidewire receiving lumen. The method further includes retracting an active fixation mechanism disposed at a lead distal end portion via rotation of the driver proximal end in substantially a single (e.g., counterclockwise) direction. Several options for extracting a lead from a subject are as follows. In one example, rotating the driver proximal end in substantially the single direction affects extractable engagement of the driver distal end with an active fixation mechanism proximal end. In yet another example, extracting the lead from the subject includes engaging the driver distal end with the lead distal end portion, and applying an extraction force to the driver proximal end.

The assemblies, apparatuses, and methods described herein provide numerous advantages over conventional lead designs including combining the benefits of a co-radial pacing lead (i.e., small lead body size resulting in low blood flow obstruction, small wounds, and low risk of pneumothorax) with those of an extendable/retractable lead (i.e., active fixation of a lead distal end or intermediate portion at a desired location within, on, or about a subject's heart as determined by an implanting physician and the ability to expose/hide a corkscrew during implantation). Co-radial lead constructions allow for a smaller diameter lead body than co-axial lead constructions, for example, by eliminating the outer coil of the traditional co-axial lead design. Another advantage of the present assemblies, apparatuses, and methods includes providing a lead design that feels like a terminal-driven extendable/retractable lead design (i.e., driven from the lead proximal end portion) to the implanting physician, but has the simplicity of a stylet-driven lead design.

Several other advantages are also made possible by the present assemblies, apparatuses, and methods. As one example, the present assemblies, apparatuses, and methods provide a lead in which the driver may be removed post-implant and therefore need not be designed with fatigue in mind. As a result, the driver may be composed of many more materials than would be the case if fatigue were an issue of concern. As another example, the present assemblies, apparatuses, and methods provide a lead that does not require a bushing to prevent conductor coil movement during the extension or retraction of the active fixation mechanism. As yet another advantage, the present assemblies, apparatuses, and methods provide for the extraction of inoperative (i.e., failed or unused) leads by allowing an extraction force to be transmitted to the lead distal end (when applied at the lead proximal end).

These and other examples, aspects, advantages, and features of the present assemblies, apparatuses, and methods described herein will be set forth in part in the detailed description, which follows, and in part will become apparent to those skilled in the art by reference to the following description of the present assemblies, apparatuses, methods, and drawings or by practice of the same.

BRIEF DESCRIPTION OF THE DRAWINGS

In the drawings, which are not necessarily drawn to scale, like numerals describe similar components throughout the several views. The drawings illustrate generally, by way of example, but not by way of limitation, various embodiments discussed in this patent document.

DETAILED DESCRIPTION

The following detailed description includes references to the accompanying drawings, which form a part of the detailed description. The drawings show, by way of illustration, specific embodiments in which the present assemblies, apparatuses, and methods may be practiced. These embodiments, which are also referred to herein as "examples," are described in enough detail to enable those skilled in the art to practice the present assemblies, apparatuses, and methods. The embodiments may be combined or varied, other embodiments may be utilized or structural or logical changes may be made without departing from the scope of the present assemblies, apparatuses, and methods. It is also to be understood that the various embodiments of the present assemblies, apparatuses, and methods, although different, are not necessarily mutually exclusive. For example, a particular feature, structure or characteristic described in one embodiment may be included within other embodiments. The following detailed description is, therefore, not to be taken in a limiting sense, and the scope of the present assemblies, apparatuses, and methods are defined by the appended claims and their equivalents.

In this document, the terms "a" or "an" are used to include one or more than one, and the term "subject" is used synonymously with the term "patient". Furthermore, it is to be understood that the phraseology or terminology employed herein, and not otherwise defined, is for the purpose of description only and not of limitation.

Assemblies, apparatuses, and methods are provided herein combining the benefits of a co-radial pacing lead with those of an extendable/retractable lead. Further, the assemblies, apparatuses, and methods provide for the extraction of inoperative (i.e., failed or unused) leads by allowing an extraction force to be transmitted to the lead distal end (when applied at the lead proximal end). In one example, a lead assembly includes a driver removably and rotatably seatable within a lead lumen. The driver is dimensioned and configured to extend or retract (i.e., actuate) an active fixation mechanism disposed at a lead distal end portion and thereafter be removed from the assembly. In another example, a lead assembly includes a driver including a driver distal end portion extractably engagable with the lead distal end portion.

Figure 1:
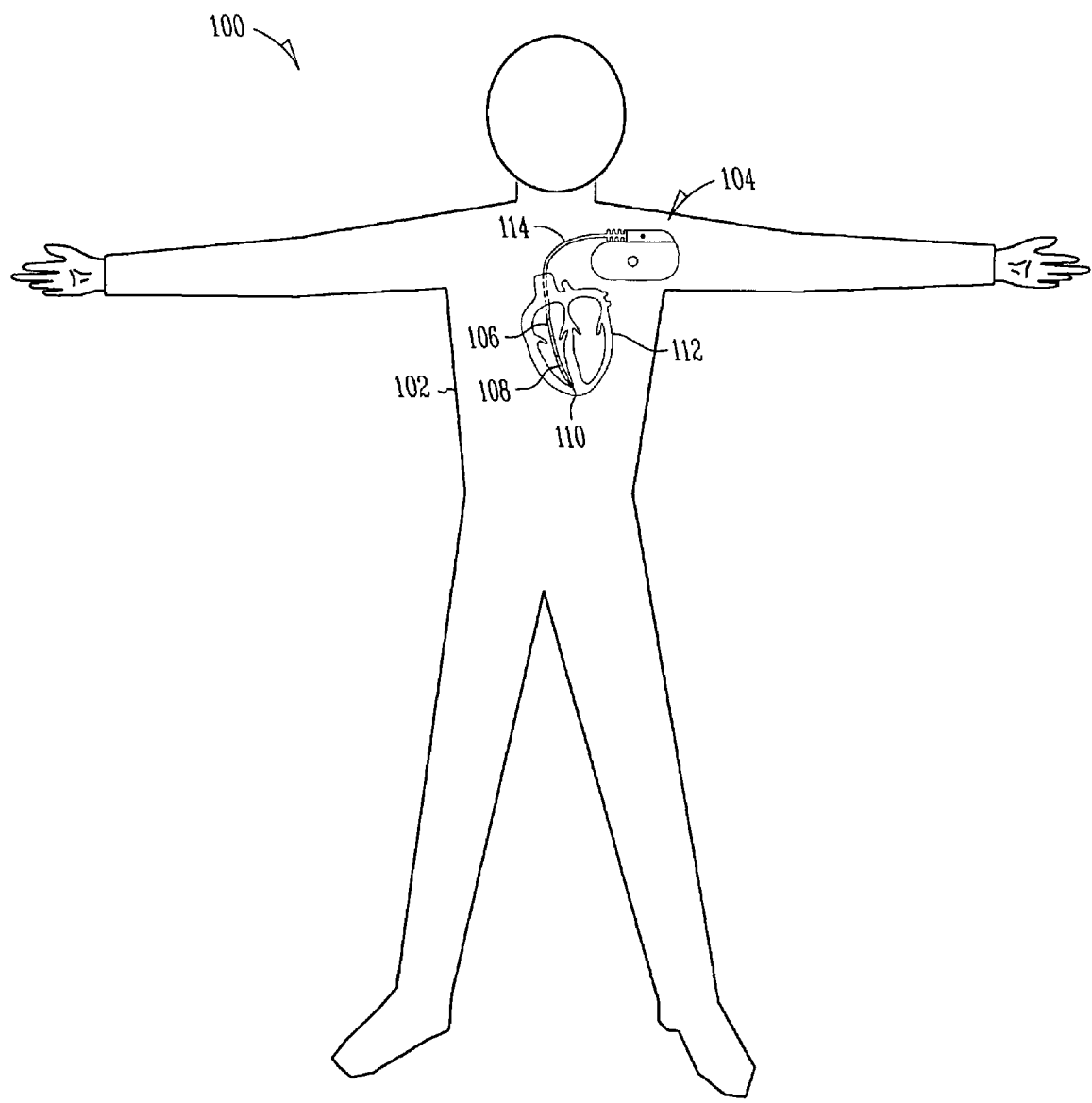
FIG. 1 is a schematic view illustrating a lead system and an environment in which the lead system may be used, as constructed in accordance with at least one embodiment.

FIG. 1 is a schematic view illustrating a lead system 100 and an environment 102 (e.g., a subject's chest) in which lead system 100 may be used. In one example, lead system 100 includes an implantable medical device (referred to as IMD) 104 and at least one lead 114 that electrically connects IMD 104 with a subject's heart 112. IMDs 104 include, among other things, cardiac rhythm management (referred to as "CRM") devices such as pacers, cardioverters, defibrillators, cardiac resynchronization therapy (referred to as "CRT") or coordination devices, and sensing instruments. In another example, lead 114 includes a proximal ring electrode 106, a distal ring electrode 108 and an active fixation mechanism 110. In the illustrative example of FIG. 1, IMD 104 is a battery-powered device that is implanted subcutaneously in the subject's chest 102 and connected to lead 114, a distal portion of which is implanted in the right atrium and right ventricle of heart 112.

Figure 2:
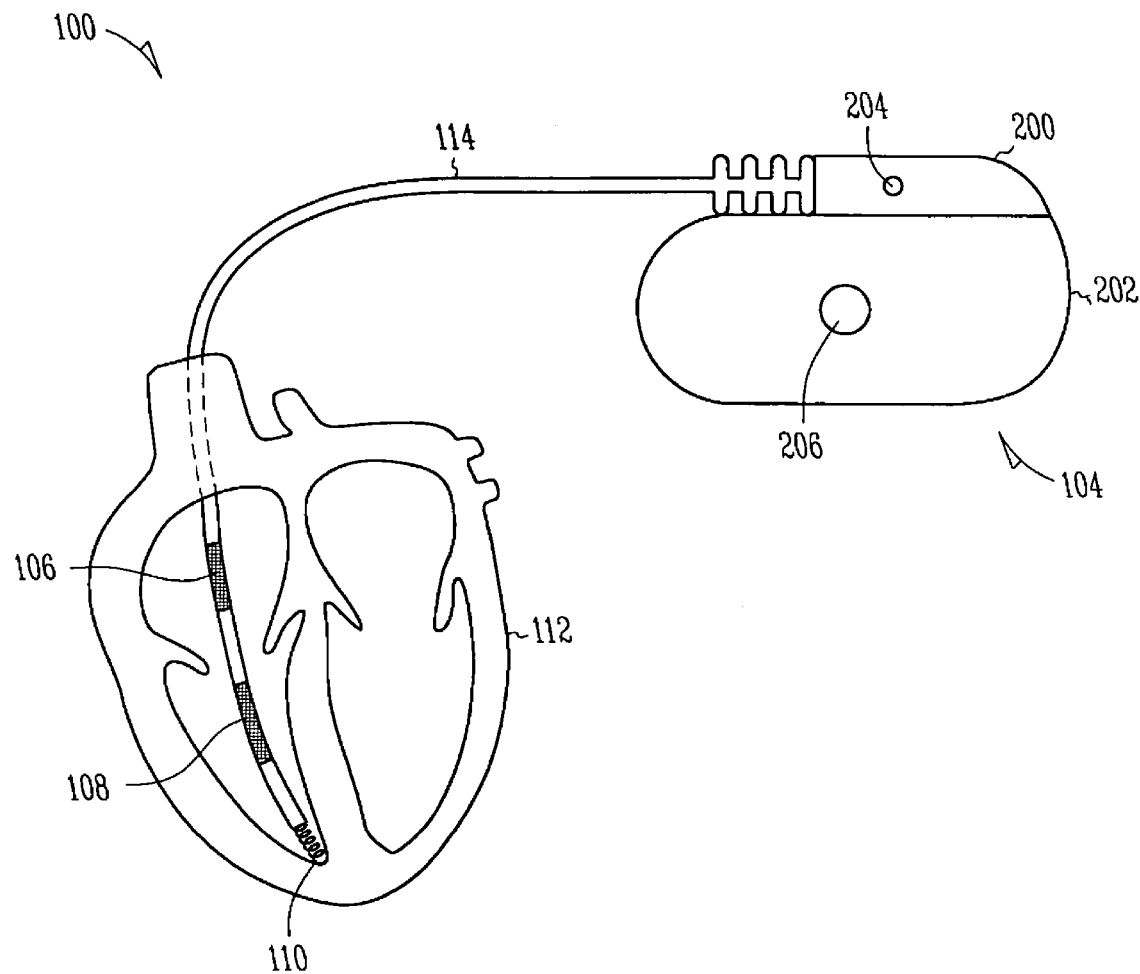
FIG. 2 is a schematic view illustrating a lead system, as constructed in accordance with at least one embodiment.

FIG. 2 is a schematic view illustrating a lead system 100 including an IMD 104 and at least one lead 114. In this example, IMD 104 is electrically coupled to a subject's heart 112 using lead 114, such as a multi-electrode lead. As shown, lead 114 includes a proximal ring electrode 106, a distal ring electrode 108, and an active fixation mechanism 110. In one example, active fixation mechanism 110 is electrically coupled with IMD 104 and thereby acts not only as a fixation mechanism, but also as an electrode. In such an example, each of proximal ring electrode 106, distal ring electrode 108, and active fixation mechanism 110 is independently electrically connected to a separate corresponding electrically conductive terminal within an insulating header 200. Header 200 is affixed to a hermetically sealed housing 202, which may be formed from a conductive metal such as titanium, and which carries, at least portions of, the electronic components of IMD 104. Housing 202 may be substantially covered over its entire surface by a suitable insulator, such as silicone rubber. In this example, header 200 includes a header electrode 204, and housing 202 includes a housing electrode 206.

Figure 3A:
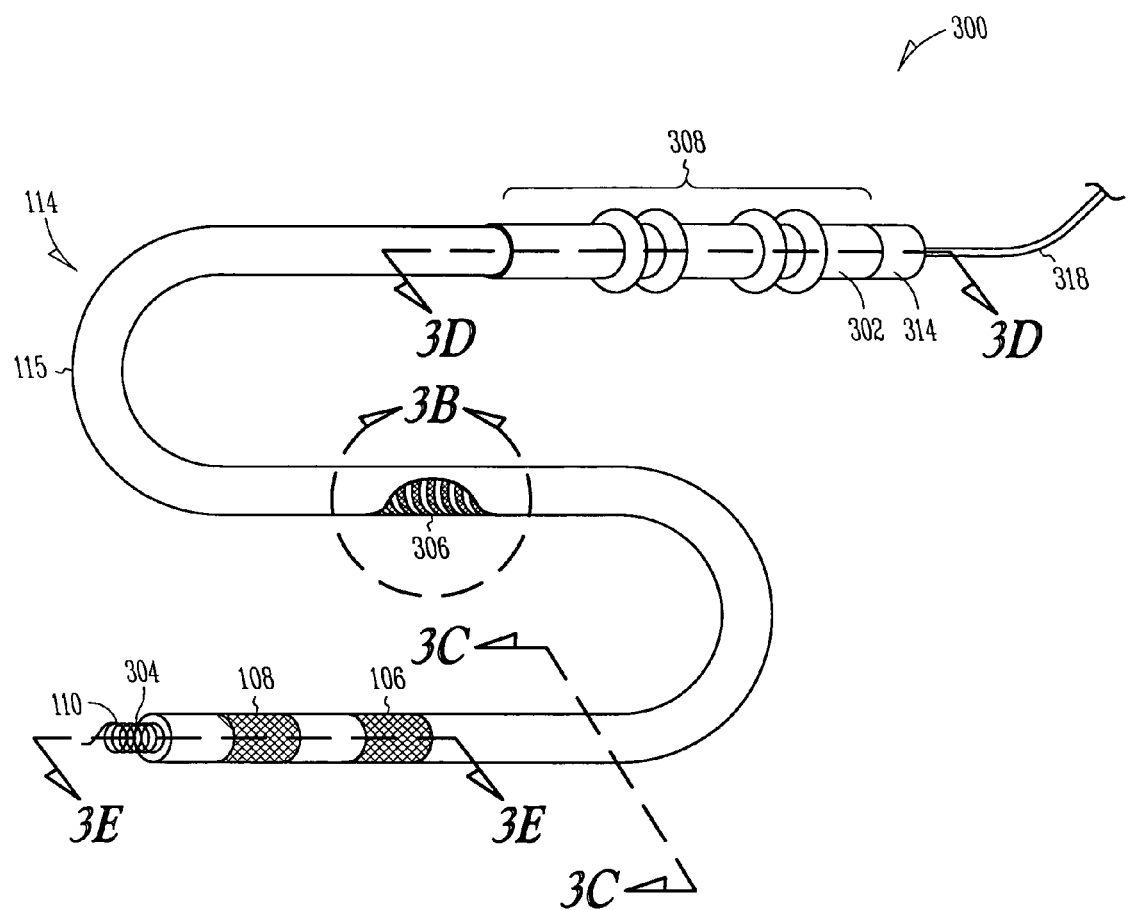
FIG. 3A is a perspective view illustrating a lead assembly, as constructed in accordance with at least one embodiment.

FIG. 3A is a perspective view illustrating a lead assembly 300 that is configured for fixation on, about, or within a subject's heart 112 (see, e.g., FIG. 2) by way of an active fixation mechanism 110. Lead assembly 300 includes a lead 114 having a lead body 115, which extends from a lead proximal end portion 302 to a lead distal end portion 304 and including at least one conductor 306 disposed therein. Lead proximal end portion 302 includes a connector 308 for electrical connection to an IMD 104 (FIGS. 1, 2). As discussed above, IMD 104 may include, among other things, cardiac rhythm management (CRM) devices such as pacers, cardioverters, defibrillators, cardiac resynchronization therapy (CRT) or coordination devices, and sensing instruments. In this example, active fixation mechanism 110 is disposed at lead distal end portion 304 and is dimensioned and configured to be extendable from or retractable within lead 114, in particular lead body 115 (see, e.g., FIGS. 6A, 6B). As shown, lead distal end portion 304 further includes a proximal ring electrode 106 and a distal ring electrode 108.

Figure 3B:
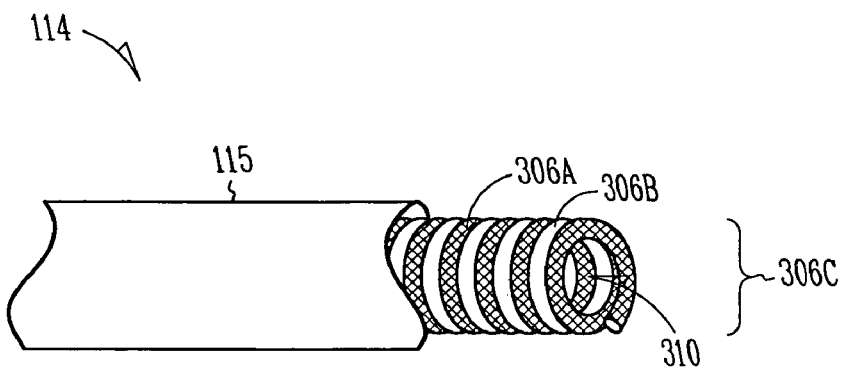
FIG. 3B is a perspective view illustrating portions of the lead assembly of FIG. 3A, as constructed in accordance with at least one embodiment.
Figure 3C:
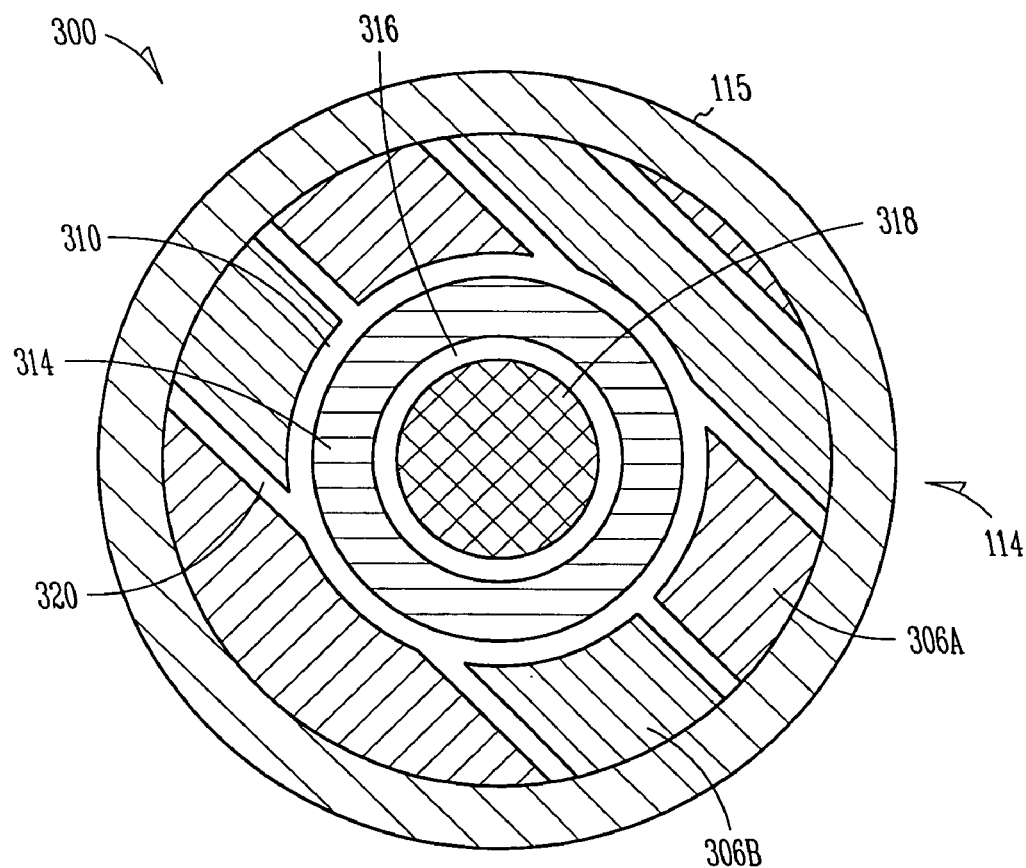
FIG. 3C is a sectional view taken along line 3C-3C of FIG. 3A, as constructed in accordance with at least one embodiment.
Figure 3D:
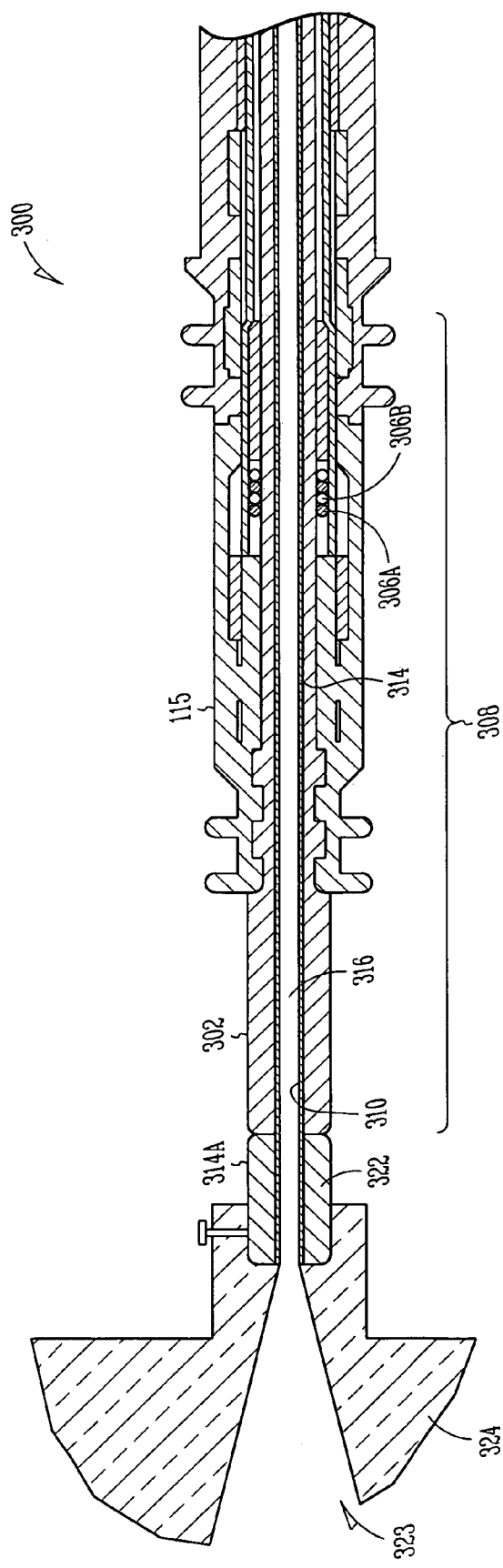
FIG. 3D is a sectional view taken along line 3D-3D of FIG. 3A further including an additional element, as constructed in accordance with at least one embodiment.
Figure 3E:
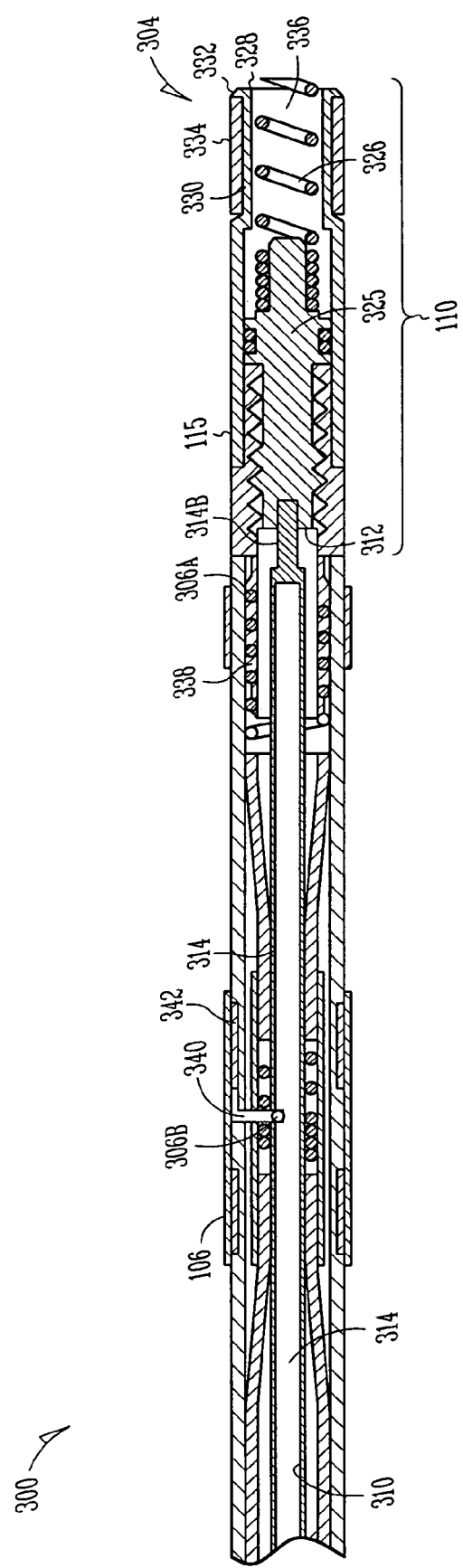
FIG. 3E is a sectional view taken along line 3E-3E of FIG. 3A, as constructed in accordance with at least one embodiment.

Within lead 114, in particular lead body 115, a lead lumen 310 (FIGS. 3B, 3C) extends from lead proximal end portion 302 to at least an active fixation mechanism proximal end 312 (FIG. 3E). In one example, lead lumen 310 (FIGS. 3B, 3C) is formed by the at least one conductor 306 (see, e.g., FIG. 3B in which co-radial conductors 306A, 306B combine to form lead lumen 310). Lead lumen 310 provides a void into which a driver 314, a proximal end of which is shown in FIG. 3A, may be removably and rotatably seated. In varying examples, driver 314 includes a stylet or guidewire receiving lumen 316 (FIG. 3C) therein. A stylet 318 or a guidewire are typically used by an implanting physician for spatial manipulation of lead assembly 300 as lead 114 is introduced into a subject. In one such example, stylet 318 is a J-shaped stylet (i.e., a pre-formed J-shaped stylet that is typically used for atrium lead placement). In another such example, stylet 318 is of cylindrical design. In yet another such example, stylet 318 is fabricated from one or more materials commonly used for stylets, such as stainless steel, titanium, or other like materials.

FIG. 3B is a perspective view illustrating portions of lead assembly 300 of FIG. 3A, such as lead 114. In varying examples, lead 114 may include two or more co-radial conductors disposed within lead body 115. As shown, lead 114 includes a first conductor 306A and a second conductor 306B, in which first conductor 306A is co-radial with second conductor 306B; that is, first conductor 306A and second conductor 306B are individually insulated conduction wires wound together to form a single (co-radial) conductor coil 306C. One of the reasons that co-radial lead designs do not easily lend themselves to actuation of an active fixation mechanism 110 (FIG. 3A) stems from first conductor 306A and second conductor 306B being wound together to form a single conductor coil 306C. Although co-radial lead designs do not easily lend themselves to actuation of active fixation mechanisms 110 (FIG. 3A), such lead designs do advantageously provide for smaller diameter lead bodies than are possible with other conventional lead configurations. In this example, lead lumen 310 is formed, at least in part, by the two co-radial conductors 306A, 306B.

FIG. 3C is a sectional view taken along line 3C-3C of FIG. 3A illustrating a cross-section of lead assembly 300. In this example, lead 114 consists of co-radial conductors 306A, 306B, each of which are surrounded by a co-extensive insulating sleeve 320 and further insulated by lead body 115 on the exterior of the co-radial conductor coil 306C (FIG. 3B). Insulation sleeve 320 is designed to provide biocompatible electrical insulation for co-radial conductors 306A, 306B, while providing an external surface that has a low coefficient of friction relative to driver 314. As shown, first conductor 306A and second conductor 306B combine to form lead lumen 310. Within lead lumen 310, driver 314 is removably and rotatably seated. In varying examples, driver 314 includes stylet or guidewire receiving lumen 316.

Although a co-radial lead 114 including two conductors 306A, 306B and a single lead lumen 310 is illustrated in FIGS. 3B-3C, the assemblies, apparatuses, and methods described herein are not so limited. In one example, lead 114 may be of co-axial design. In another example, lead 114 may include multiple lead lumens 310. In yet another example, lead 114 may include more than or less than two conductors 306A, 306B. In one such example, lead 114 may include only one conductor 306A or 306B (i.e., for a unipolar application).

FIG. 3D is a sectional view taken along line 3D-3D of FIG. 3A illustrating a cross-section of lead assembly 300, such as lead proximal end portion 302 of lead body 115. Lead proximal end portion 302 includes connector 308 for electrical connection to IMD 104 (FIGS. 1, 2). Within lead body 115, lead lumen 310 extends from lead proximal end portion 302 to at least active fixation mechanism proximal end 312 (FIG. 3E). In this example, lead lumen 310 is formed, at least in part, by the two or more co-radial conductors 306A, 306B. Lead lumen 310 provides a void into which driver 314 may by removably and rotatably seated. In varying examples, driver 314 includes a driver body extending from a driver proximal end 314A to a driver distal end 314B (FIG. 3E) and having a stylet or guidewire receiving lumen 316 therein.

Driver 314 may be designed in a number of ways. In one example, driver 314 has a tubular design; that is, an exterior cylindrical shape with a lumen 316 disposed therein. In another example, driver 314 is composed of one or a combination of a metal, such as MP35N or 316L stainless steel, and a polymer, such as polyethylene terephthalate (referred to as "PET"), polyimide, polyethylene tetrafluoroethylene (referred to as "ETFE"), polytetrafluoroethylene (referred to as "PTFE"), or polyurethane. MP35N is a registered trademark of SPS Technologies. In one such example, the driver is composed of a coiled or a braided metal wire co-extruded with a polymer. In yet another example, driver proximal end 314A includes a pin 322 portion couplable with a rotation facilitating tool 324, such as a tool manufactured by Guidant Corporation having Model No. 6616. As shown, rotation facilitating tool 324 includes a stylet introductory cavity 323 to facilitate insertion of stylet 318 (FIG. 3A) or a guidewire into stylet or guidewire receiving lumen 316. In another example, rotation facilitating tool 324 is incorporated (i.e., composed of a one-piece member) with driver 314. Still another option for driver 314 includes a driver distal end 314B (FIG. 3E) detachably matable with active fixation mechanism proximal end 312.

FIG. 3E is a sectional view taken along line 3E-3E of FIG. 3A illustrating a cross-section of lead assembly 300, such as lead distal end portion 304 of lead body 115. As shown, driver 314 is removably and rotatably seated within lead lumen 310, which extends from lead proximal end portion 302 (FIG. 3D) to active fixation mechanism proximal end 312. In this example, active fixation mechanism 110 includes a fixation actuator 325 on a proximal end coupled with a corkscrew 326 on a distal end. Driver distal end 314B includes a portion detachably matable with active fixation proximal end 312. In this way, rotation of driver 314 causes active fixation mechanism 110 to also rotate. As shown, driver distal end 314B includes a portion resembling a flat-head screwdriver, which mates with a closely-toleranced female feature on active fixation mechanism proximal end 312. In another example, driver distal end 314B includes a portion resembling a Phillips-head screwdriver, which mates with a closely-toleranced female feature on active fixation mechanism proximal end 312. In yet another example, driver distal end 314B includes a portion resembling an Allen-wrench (i.e., a hexagonal configuration), which mates with a closely-toleranced female feature on active fixation mechanism proximal end 312. Other various portions (i.e., geometries) for driver distal end 314B and active fixation mechanism proximal end 312 may also be used to detachably mate the same without departing from the scope of the assemblies, apparatuses, and methods discussed herein.

In this example, lead body 115 includes at least two electrodes at or near lead distal end portion 304 to communicate electrical signals from IMD 104 (FIGS. 1, 2) to heart 112 (FIGS. 1, 2) or other tissue of a subject. As illustrated in FIG. 3E, a tubular electrode 328 has a proximally projecting diameter portion 330 which defines a projecting annular shoulder 332 located near the distal end of tubular electrode 328. An insulating sleeve 334 is secured to the exterior of reduced diameter portion 330 and abuts against annular shoulder 332. A distal end of tubular electrode 328 includes an opening 336 through which corkscrew 326 may extend or retract.

A tubular crimp slug 338 is disposed inside tubular electrode 328. A distal end of conductor 306A is looped around a proximal end of tubular crimp slug 338. In this example, the distal end of conductor 306A is secured by crimping tubular crimp slug 338 as shown. Prior to crimping, most of the insulating sleeve (i.e., lead body 115 and insulation 320—see, FIG. 3C) should be removed from the distal end of conductor 306A to expose the conductor wire therewithin and to provide an electrical pathway to tubular electrode 328. In addition on relying on crimping to secure the distal end of conductor 306A to tubular crimp slug 338, spot or laser welding may also be employed to provide an additional attachment mechanism.

Referring still to FIG. 3E, a proximal ring electrode 106 is disposed over lead body 115. To establish electrical connection between conductor 306B and proximal ring electrode 106, conductor 306B is projected through an opening 340 in lead body 115 located in that portion of lead body 115 covered by proximal ring electrode 106. Most of the insulating sleeve (i.e., lead body 115 and insulation 320—see, FIG. 3C) should be removed from the distal end of conductor 306B to expose the conductor wire therewithin and to provide an electrical pathway to proximal ring electrode 106. The bare conductor wire of conductor 306B is sandwiched between the exterior of an annular element 342 and the interior of proximal ring electrode 106.

Prior to installing proximal ring electrode 106, the bare conductor wire of conductor 306B may be secured to annular member 342 by laser or spot welding. After the laser or spot welding takes place, proximal ring electrode 106 is positioned and tight-fitted (e.g., swaged). The tight-fitting serves to reduce the diameter of proximal ring electrode 106 and to ensure physical contact between proximal ring electrode 106 and the conductor wire of conductor 306B or annular member 342.

Figure 4A:
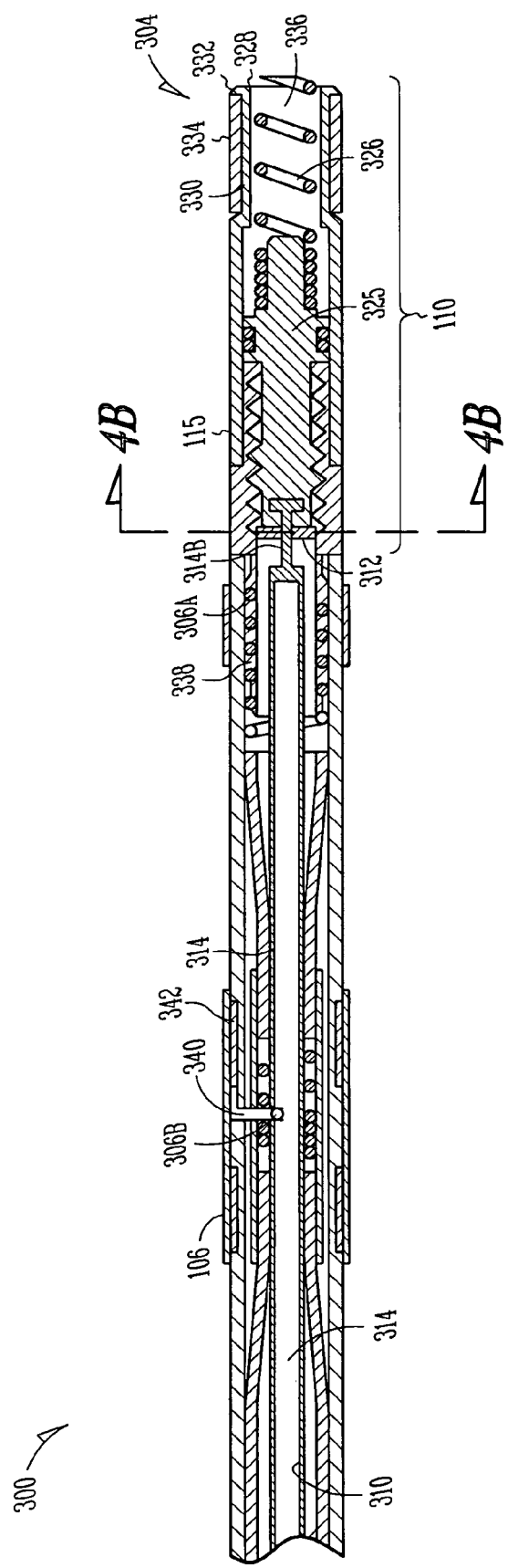
FIG. 4A is a sectional view taken along line 3E-3E of FIG. 3A, as constructed in accordance with another embodiment.

FIG. 4A is a sectional view, similar to FIG. 3E, illustrating another example of a driver distal end 314B portion. In this example, like FIG. 3E, a driver 314 is removably and rotatably seated within a lead lumen 310, which extends from a lead proximal end portion 302 (FIG. 3D) to an active fixation mechanism proximal end 312. Also like FIG. 3E, FIG. 4A illustrates an active fixation mechanism 110 including a fixation actuator 325 on a proximal end coupled with a corkscrew 326 on a distal end.

Unlike FIG. 3E, however, this example includes a driver 314 having a driver distal end 314B portion dimensioned and configured to not only actuate active fixation mechanism 110, but also extractably engage with a lead distal end portion 304, such as via active fixation mechanism proximal end 312. The extractable engagement between driver distal end 314B and lead distal end portion 304 advantageously allows a (lead) extraction force to be transmitted to a lead distal end portion 304 (rather than a lead proximal end portion 302), thereby reducing the possibility that lead body 115 (FIG. 3A) will stretch, tear, or break as a result of the force application. In another example, a stylet having a stylet distal end portion dimensioned and configured to actuate active fixation mechanism 110 and extractably engage with a lead distal end portion 304 is used in place of driver 314.

Figure 4B:
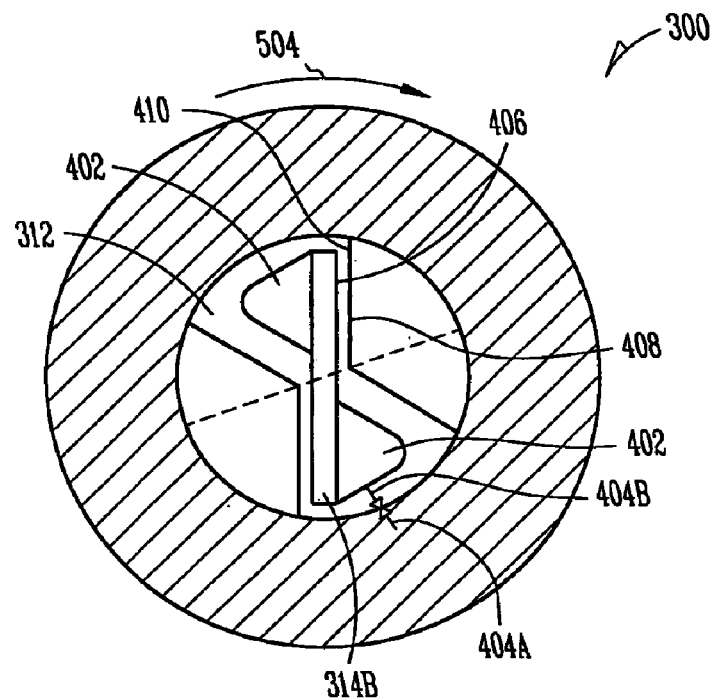
FIG. 4B is a sectional view taken along line 4B-4B of FIG. 4A, as constructed in accordance with at least one embodiment.
Figure 4C:
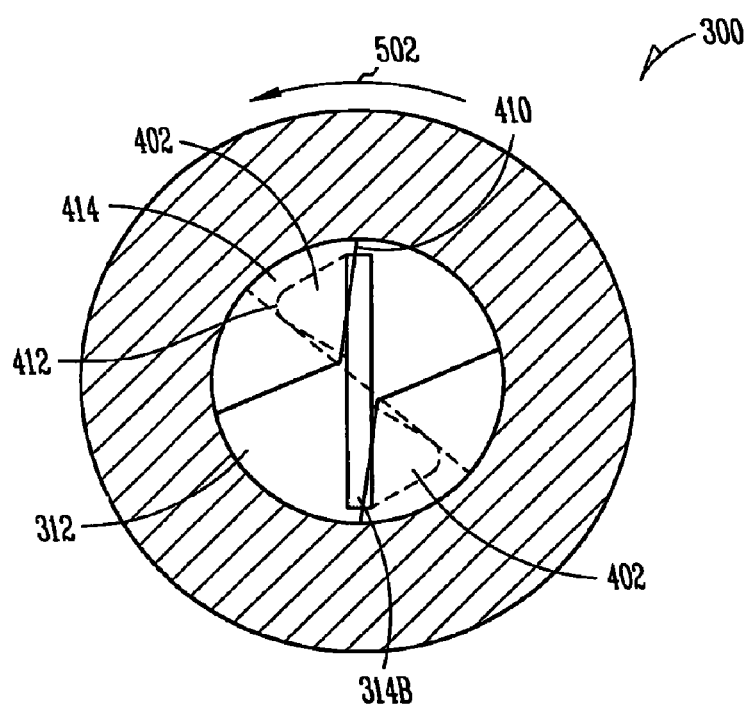
FIG. 4C is a sectional view taken along line 4B-4B of FIG. 4A, as constructed in accordance with another embodiment.

FIGS. 4B and 4C are sectional views taken along line 4B-4B of FIG. 4A illustrating a cross-section of lead assembly 300, such as an extractable engagement between a portion of driver distal end 314B and lead distal end portion 304 (FIG. 4A) (e.g., via active fixation mechanism proximal end 312). Specifically, FIG. 4B illustrates (detachable) engagement between driver distal end 314B and active fixation mechanism proximal end 312 when driver 314 (FIG. 4A) is rotated in a first (e.g., clockwise) direction 504, while FIG. 4C illustrates (extractable) engagement between driver distal end 314B and active fixation mechanism proximal end 312 when driver 314 is rotated in a second (e.g., counterclockwise) direction 502.

Referring first to FIG. 4A, driver distal end 314B includes a portion resembling a flat-head screwdriver, and further including at least one arched-shaped protrusion 402 extending from each side thereof. As shown, active fixation mechanism proximal end 312 is dimensioned and configured to matably receive driver distal end 314B at a predetermined alignment (e.g., alignment of arrows 404A and 404B). Upon the mating of driver distal end 314B and active fixation mechanism proximal end 312, rotation of driver 314 (FIG. 4A) in first direction 504 causes actuation of active fixation mechanism 110 (FIG. 4A), such as extension of corkscrew 326 (FIG. 4A) from lead body 115 (FIG. 4A). As shown, rotation of driver 314 (FIG. 4A) in first direction 504 results in edge 406 of driver distal end 314B contacting edge 408 of stepped portion 410 of active fixation mechanism proximal end 312, thereby transmitting rotation force to active fixation mechanism 110.

Referring now to FIG. 4B, (extractable) engagement between driver distal end 314B and active fixation mechanism proximal end 312 resulting from rotation of driver 314 (FIG. 4A) in second direction 502 is shown. In this example, rotation of driver 314 (FIG. 4A) in second direction 502 results in protruding edge 412 of driver distal end 314B being inserted into cavity 414 of stepped portion 410 (of active fixation mechanism proximal end 312). Upon insertion of protruding edge 412 into cavity 414, driver 314 (FIG. 4A) is prohibited from being extracted from lead 114 (FIG. 3A) (i.e., driver 314 is extractably engaged with active fixation mechanism proximal end 312). Other mechanical locking configurations (than those discussed above) between driver distal end 314B and lead distal end portion 304, such as active fixation mechanism proximal end 312, may also used to actuate active fixation mechanism 110 and extractably engage driver 314 and lead proximal end 304 without departing from the scope of the assemblies, apparatuses, and methods discussed herein. In addition, the extractable engagement between driver 314 and lead proximal end 304 may be of a type including balloon expansion, mesh expansion, or other like engagement means. Moreover, as alluded to above, a stylet having a stylet distal end portion including one of the foregoing extractable engagement configurations may be used in place of driver 314 (FIG. 4A) without departing from the scope of the assemblies, apparatuses, and methods discussed herein.

Figure 5:
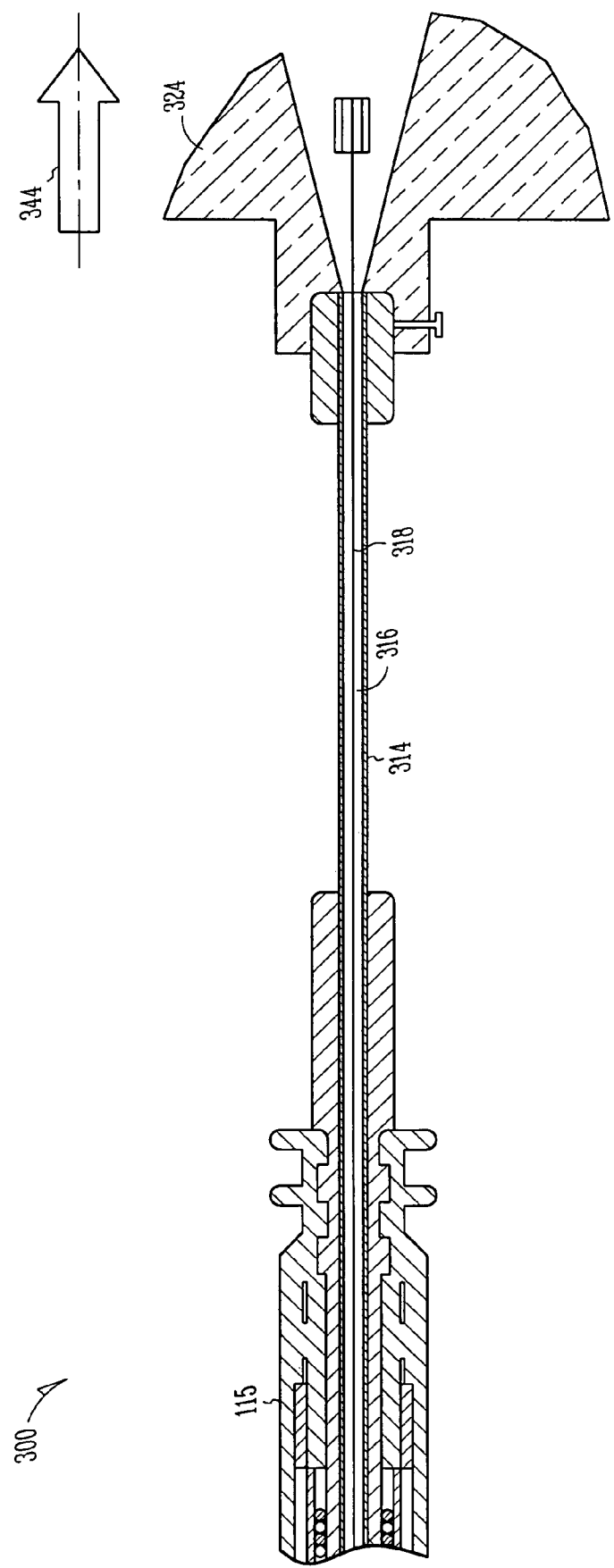
FIG. 5 is a sectional view of portions of the lead assembly of FIG. 3D, as constructed in accordance with at least one embodiment.

FIG. 5 is a sectional view of a portion of a lead assembly 300. After a driver 314 activates or de-activates (i.e., extends or retracts, respectively) an active fixation mechanism 110 (FIGS. 3A, 3E), driver 314 may be removed from lead body 115 and discarded. In this example, driver 314 is shown being removed from lead body 115 by exerting a force on rotation facilitating tool 324 in a direction 344 away from lead body 115. The removability of driver 314 is advantageous in that post-implant fatigue issues need not be dealt with for driver 314. As a result, driver 314 may be composed of many more materials than would be possible if fatigue were an issue of concern. The removal of driver 314 (from lead body 115) further allows lead body 115 to be free of any non-functioning components which could fail over time. In this example, a stylet 318 (FIG. 3A) is shown disposed in a stylet or guidewire receiving lumen 316. In another example, removal of driver 314 results in the simultaneous removal of stylet 318 (i.e., if stylet 318 has not been previously removed).

Figure 6A:
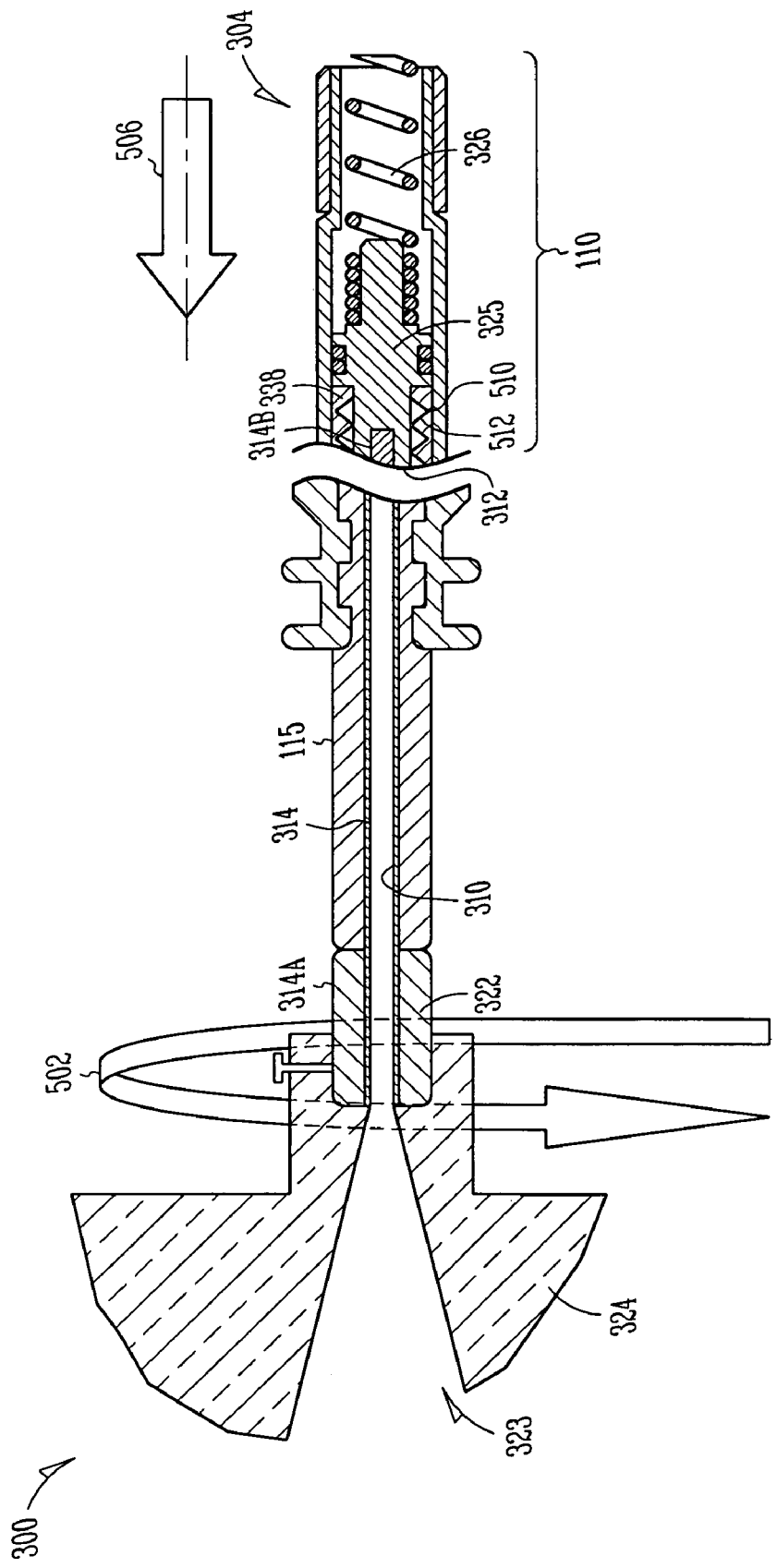
FIG. 6A is a sectional view of portions of the lead assembly of FIGS. 3D and 3E, as constructed in accordance with at least one embodiment.
Figure 6B:
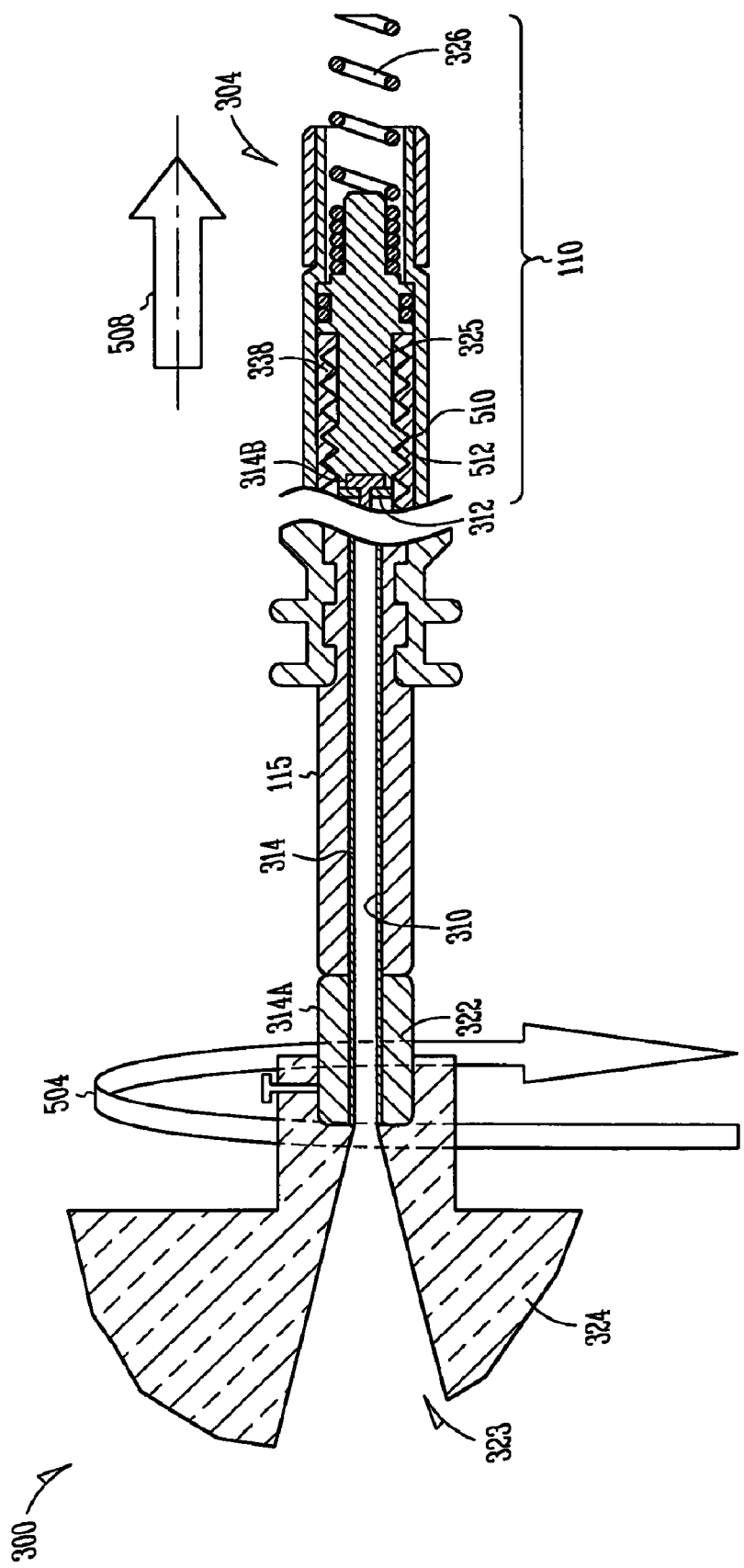
FIG. 6B is a sectional view of portions of the lead assembly of FIGS. 3D and 3E, as constructed in accordance with at least one embodiment.

FIGS. 6A and 6B are sectional views of a lead assembly 300. In particular, FIG. 6A illustrates the retraction of an active fixation mechanism 110 within a lead body 115, while FIG. 6B illustrates the extension of an active fixation mechanism 110 from lead body 115. In these examples, lead body 115 includes a lead lumen 310 into which a driver 314 is removably and rotatably seated. Driver 314 includes a driver body extending from a driver proximal end 314A to a driver distal end 314B. Driver proximal end 314A, as shown, includes a pin 322 portion that is rotatable without affecting movement of two or more co-radial conductors 306A, 306B (FIGS. 3D, 3E). Pin 322 portion is dimensioned and configured to couple with a rotation facilitating tool 324, such as a tool manufactured by Guidant Corporation having Model No. 6616, or be integrated (i.e., formed of one-piece) with a knob or a handle. Driver distal end 314B includes a portion detachably matable with an active fixation mechanism proximal end 312 (FIG. 6B).

In these examples, active fixation mechanism 110 includes a fixation actuator 325 on a proximal end 312 coupled with a corkscrew 326 on a distal end. The mating relationship between driver distal end 314B and active fixation mechanism proximal end 312 allows rotation of driver 314 to affect rotation of active fixation mechanism 110. As shown in the illustrative example of FIG. 6B, rotation of driver 314 in a first (e.g., clockwise) direction 504 affects extension of active fixation mechanism 110, in particular corkscrew 326, from lead body 115 (i.e., in direction 508). As shown in the illustrative example of FIG. 6A, rotation of driver 314 in a second (e.g., counterclockwise) direction 502 affects retraction of active fixation mechanism 110, in particular corkscrew 326, within lead body 115 (i.e., in direction 506).

As shown, active fixation mechanism 110 includes fixation actuator 325 and corkscrew 326. It is the rotation of driver 314, which in turn causes fixation actuator 325 to rotate; that is, assuming driver distal end 314B is detachably mated (i.e., engaged) with the fixation actuator proximal end. As shown, fixation actuator 325 includes external threads 510, which are dimensioned and configured to interact with internal threads 512 of tubular crimp slug 338. Through the interaction between external threads 510 of fixation actuator 325 and internal threads 512 of tubular crimp slug 338, corkscrew 326 is caused to rotate and translate (e.g., move horizontally). When the corkscrew 326 is extended from lead body 115, it is dimensioned and configured to substantially fix a location of lead distal end portion 304 within, on, or about a subject's heart 112 (FIGS. 1, 2) as desired by an implanting physician. When the corkscrew 326 is retracted within lead body 115, it is dimensioned and configured so as to not expose the (sharpened) corkscrew 326. The retraction of corkscrew 326 may be advantageous when lead 114 (FIGS. 2, 3A) is being introduced through a blood vessel into heart 112 (FIGS. 1, 2) (i.e., when lead 114 is being implanted) or when the implanting physician desires to re-locate the position of lead distal end portion 304.

Figure 7:
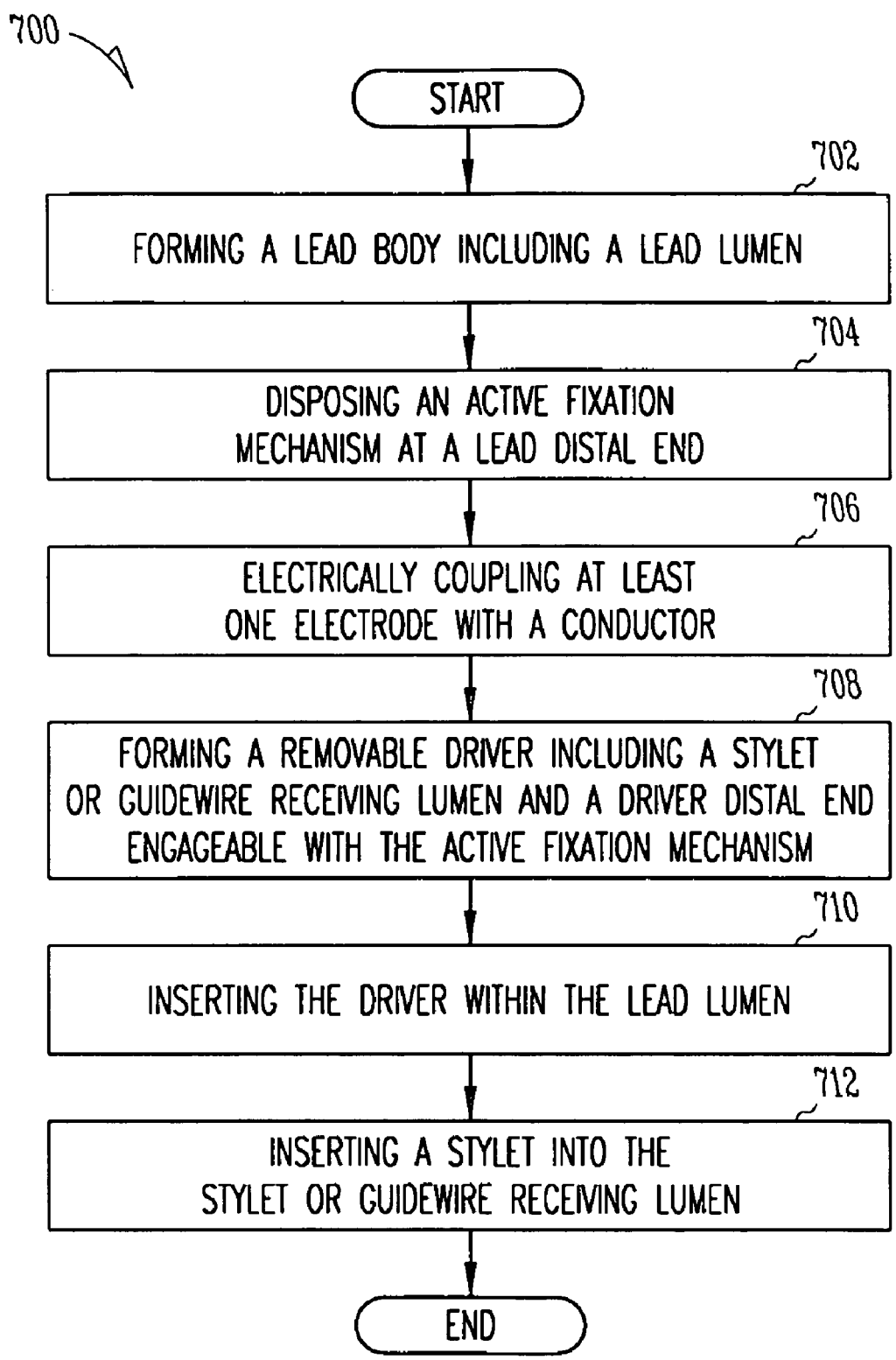
FIG. 7 is a flow diagram illustrating a method for manufacturing a lead assembly, as constructed in accordance with at least one embodiment.

FIG. 7 is a flow diagram illustrating a method 700 for manufacturing a lead assembly. At 702, a lead body extending from a lead proximal end portion to a lead distal end portion is formed. Forming the lead body further includes forming a lead lumen disposed therein. In one example, forming the lead lumen includes positioning two or more co-radial conductors within the lead body. As discussed above, a first and a second individually insulated conductor may be wound together to form a single co-radial conductor coil. As also discussed, it may be within this conductor coil that the lead lumen exists.

At 704, an extendable and retractable active fixation mechanism is disposed at the lead distal end portion. In one example, disposing the active fixation mechanism at the lead distal end portion includes coupling a corkscrew to a distal end of a fixation actuator. In such an example, the active fixation mechanism includes, among other things, the fixation actuator and the corkscrew. At 706, at least one electrode is electrically coupled with a conductor (e.g., the first or the second conductor forming the single co-radial conductor coil) located within the lead body. In this way, electrical signals sent from an IMD may be communicated to heart or other tissue at or near the location of the at least one electrode.

At 708, a longitudinally extending removable driver is formed. Forming the longitudinally extending removable driver includes forming a stylet or guidewire receiving lumen therein, and further includes forming a driver distal end portion detachably matable with an active fixation mechanism proximal end. In one example, the driver distal end portion is detachably matable with a fixation actuator proximal end, which as discussed above, may be coupled with the corkscrew on its distal end to comprise the active fixation mechanism. In another example, forming the driver includes forming a driver distal end portion extractably engagable with the lead distal end portion. In yet another example, forming the driver further includes forming a driver proximal end including a pin portion. The pin portion is rotatable without affecting movement of the co-radial conductor coil. In another example, a rotation facilitating tool may be coupled to the pin portion to facilitate in the rotation of the driver, and thus the actuation of the active fixation mechanism.

At 710, the longitudinally extending removable driver is inserted into the lead lumen. In one example, the lead lumen is dimensioned and configured to removably and rotatably seat the driver. At 712, a stylet is inserted into the stylet or guidewire receiving lumen. In one example, the lead assembly is packaged with the driver already inserted within the lead lumen and the stylet already inserted within the stylet or guidewire receiving lumen (i.e., pre-loaded with the driver and the stylet). In another example, the lead assembly is pre-loaded with the driver, but not the stylet.

Figure 8:
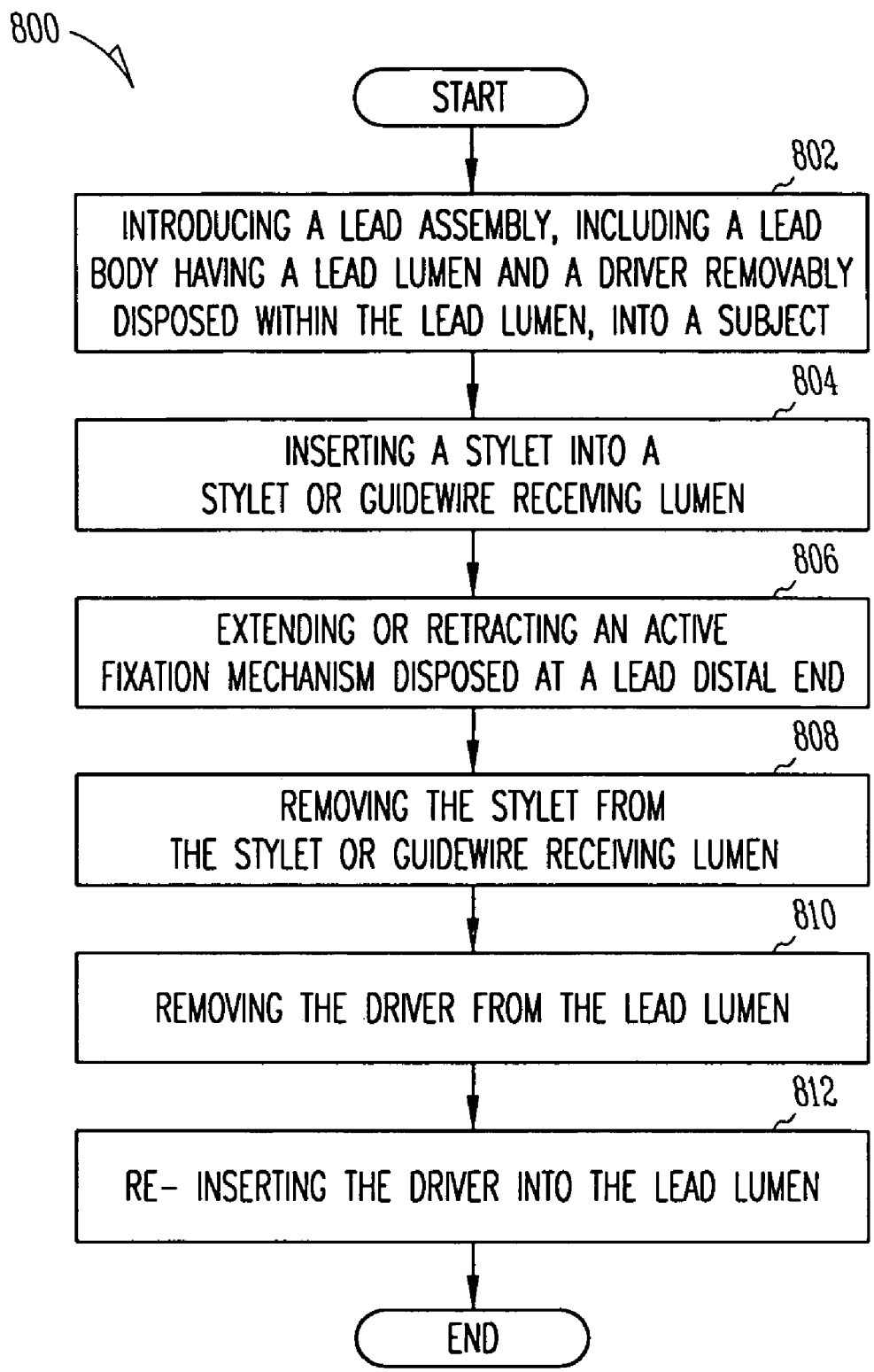
FIG. 8 is a flow diagram illustrating a method for installing a lead, as constructed in accordance with at least one embodiment.

FIG. 8 is a flow diagram illustrating a method 800 for installing a lead. At 802, a lead assembly is introduced into a subject. In one example, the lead assembly introduced into the subject includes a lead body extending from a lead proximal end portion to a lead distal end portion and having a lead lumen disposed therein. In another example, the lead assembly includes a driver, including a stylet or guidewire receiving lumen, removably and rotatably disposed within the lead lumen. At 804, a stylet is inserted into the stylet or guidewire receiving lumen; however, the stylet may be inserted into such lumen before the lead assembly is introduced into the subject.

At 806, an active fixation mechanism disposed at the lead distal end portion is actuated. In one example, the actuation includes extension or retraction of the active fixation mechanism from or within the lead body, respectively. In another example, the actuation is made possible by way of detachable engagement (e.g., a mating relationship) between a driver distal end and an active fixation mechanism proximal end. In one such example, the driver distal end includes a portion resembling a flat-head screwdriver, which interfaces with a closely-toleranced female feature on the active fixation mechanism proximal end. In another such example, the driver distal end includes a portion resembling a Phillips-head screwdriver, which interfaces with a closely-toleranced female feature on the active fixation mechanism proximal end. In yet another such example, the driver distal end includes a portion resembling an Allen-wrench (i.e., a hexagonal configuration), which interfaces with a closely-toleranced female feature on the active fixation mechanism proximal end. Other various portions (i.e., geometries) for the driver distal end and the active fixation mechanism proximal end may also be used to detachably engage the same without departing from the scope of the assemblies, apparatuses, and methods described herein.

In varying examples, the extension or retraction of the active fixation mechanism includes selectively rotating a driver proximal end in a first (e.g., clockwise) or a second (e.g., counterclockwise) direction. In one such example, rotating the driver proximal end in the first direction affects extension of the active fixation mechanism from the lead body (i.e., for a "right-handed" corkscrew). In another such example, rotating the driver proximal end in the second direction affects retraction of the active fixation mechanism within the lead body (i.e., for a "right-handed" corkscrew). In yet another such example, rotating the driver proximal end in either the first or the second direction does not affect movement of a co-radial conductor coil disposed within the lead body. Rotation of the driver proximal end may be facilitated by the coupling of a rotation facilitating tool to the driver proximal end, such as a pin. As one example, the rotation facilitating tool affixed to the driver proximal end may be a tool manufactured by Guidant Corporation, such as Model No. 6616, or a knob or handle incorporated with the driver proximal end.

At 808, the stylet is removed from the stylet or guidewire receiving lumen. After the lead has been positioned within the subject as desired by the implanting physician, the stylet is removed. At 810, the driver is removed from the lead lumen. After the lead is positioned as desired and the active fixation mechanism has been activated (i.e., coupled to the desired heart or other tissue) using the driver, the driver may then be removed from the lead lumen. In one example, the stylet and the driver are removed simultaneously (i.e., if the stylet has not been previously removed). Such simultaneous removal is made possible by exerting a removal force on the driver, which in many examples, houses the stylet therein. As a result, the stylet is removed upon removal of the driver.

At 812, the driver is re-inserted. In one example, the implanting physician may desire to adjust the position of the lead within the subject after an initial placement. To facilitate such re-location, the driver may be re-inserted into the lead lumen to de-activate the active fixation mechanism (i.e., retract the active fixation mechanism into the lead body) and subsequently re-activate the active fixation mechanism (i.e., extend the active fixation mechanism from the lead body) at the newly desired location.

Figure 9:
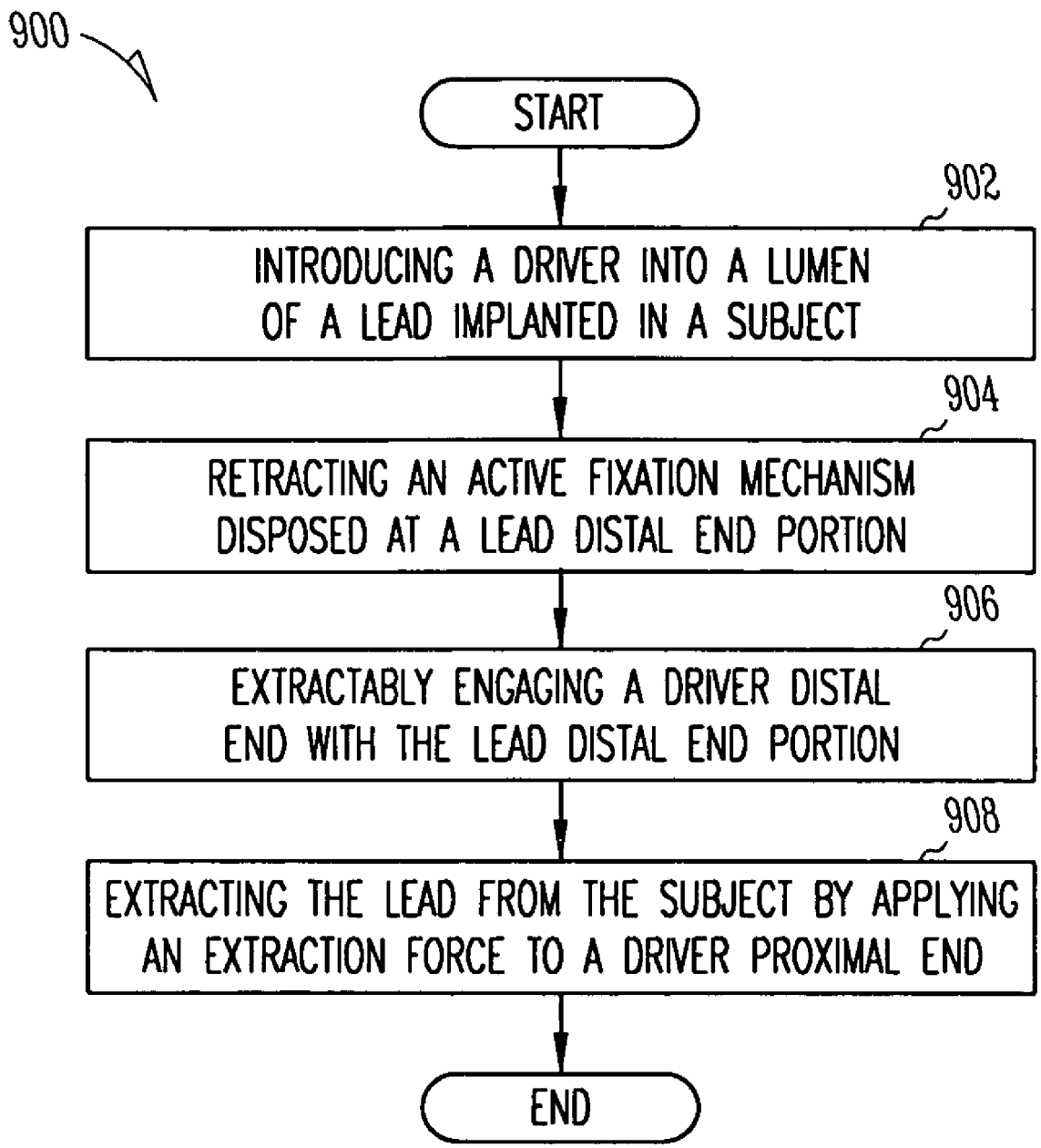
FIG. 9 is a flow diagram illustrating a method for extracting a lead, as constructed in accordance with at least one embodiment.

FIG. 9 is a flow diagram illustrating a method 900 of extracting a lead from a subject. At 902, a driver is introduced into a lead lumen. In one example, the driver introduced into the lead lumen includes a driver body extending from a driver proximal end to a driver distal end and having a stylet or guidewire receiving lumen therein. Within the stylet or guidewire receiving lumen, a stylet may be disposed to (among other things) facilitate complete insertion of the driver into the lead lumen. At 904, an active fixation mechanism disposed at a lead distal end portion is retracted. In one example, the retraction of the active fixation mechanism includes rotating a driver proximal end in substantially a single (e.g., counterclockwise for a "right-handed" corkscrew) direction. In another example, the retraction of the active fixation mechanism is made possible by way of engagement (e.g., a mating relationship) between the driver distal end and an active fixation mechanism proximal end.

At 906, the driver distal end is extractably engaged with the lead distal end portion. In one example, the rotation of the driver proximal end in substantially the single (e.g., counterclockwise) direction affects extractable engagement (i.e., mechanical locking) of the driver distal end with an active fixation mechanism proximal end. In one such example, at least one protrusion of the driver distal end is dimensioned and configured to be rotatably insertable within a cavity of the active fixation mechanism proximal end. In this example, upon the rotatable insertion of the at least one protrusion into the cavity, the driver is prohibited from being extracted from the lead (i.e., in an axial direction) by a cavity wall of the active fixation mechanism. In another example, rotation of the driver proximal end may be facilitated by the coupling or integration of a rotation facilitating tool to the driver proximal end.

At 908, the lead is extracted from the subject by the application of an extraction force to a driver proximal end. As a result of the driver configuration (i.e., the driver body extending from a driver proximal end to a driver distal end), the extraction force is transmitted to the driver distal end, which may extractably engaged with the lead distal end portion. In one example, the extractable engagement between the driver distal end and the lead distal end portion occurs by way of an active fixation mechanism. In such an example, the active fixation mechanism is coupled with the lead proximal end portion. In addition, the active fixation mechanism proximal end is dimensioned and configured to mechanically lock the driver distal end. In another example, a force handle may be attached to the driver proximal end to facilitate application of the extract force.

The assemblies, apparatuses, and methods described herein provide numerous advantages over conventional lead designs including combining the benefits of a co-radial pacing lead (i.e., small lead body size resulting in low blood flow obstruction, small wounds, and low risk of pneumothorax) with those of an extendable/retractable lead (i.e., active fixation of a lead distal end portion at a desired location within, on, or about a subject's heart as determined by an implanting physician and the ability to expose/hide a corkscrew during implantation). As one example, the assemblies, apparatuses, and methods provide a co-radial, extendable/retractable lead having a lead body 5-5.5 Fr in size. Such small diameter lead body (as compared with co-axial lead constructions, for example) is made possible in co-radial lead designs through the elimination of the outer coil of the traditional co-axial lead design. Another advantage of the assemblies, apparatuses, and methods includes providing a lead design that feels like a terminal-driven extendable/retractable lead design (i.e., driven from the lead proximal end portion) to the implanting physician, but has the simplicity of a stylet-driven lead design. Another advantage of the assemblies, apparatuses, and methods includes providing a lead design that feels like a terminal-driven extendable/retractable lead design (i.e., driven from the lead proximal end portion) to the implanting physician, but has the simplicity of a stylet-driven lead design.

Several other advantages are also made possible by the assemblies, apparatuses, and methods described herein. As one example, the assemblies, apparatuses, and methods provide a lead in which the driver may be removed post-implant and therefore need not be designed with fatigue in mind. As a result, the driver may be composed of many more materials than would be the case if fatigue were an issue of concern. As another advantage, the assemblies, apparatuses, and methods provide for the extraction of inoperative leads with by allowing an extraction force to be transmitted to the lead distal end (when applied at the lead proximal end).

It is to be understood that the above description is intended to be illustrative, and not restrictive. It should be noted that the above discusses co-radial leads with an extendable and retractable fixation mechanism and apparatus therefore; however, the present subject matter is not limited thereto. Many other embodiments will be apparent to those of skill in the art upon reviewing the above description. The scope should, therefore, be determined with reference to the appended claims, along with the full scope of equivalents to which such claims are entitled.

What is claimed is:

1. A lead assembly, comprising:
 a lead body extending from a lead proximal end portion to a lead distal end portion, the lead body including a first conductor and a second conductor disposed therein, the first conductor is co-radial with the second conductor;
 an extendable and retractable active fixation mechanism disposed at the lead distal end portion;
 a lead lumen extending within the lead body from the lead proximal end portion to at least an active fixation mechanism proximal end, the lumen at least partially formed within the outer diameter of the first and second co-radial conductors;
 a driver removably and rotatably seatable within the lead lumen, the driver including a stylet or guidewire receiving lumen therein; and
 the active fixation mechanism actuatable by rotation of the driver;
 wherein the driver is capable of being removed from the lead assembly after actuation of the active fixation mechanism.

2. The lead assembly as recited in claim 1, wherein the lead lumen is formed, at least in part, by the at least one conductor.

3. The lead assembly as recited in claim 1, wherein a driver distal end includes a portion detachably matable with the active fixation mechanism proximal end.

4. The lead assembly as recited in claim 1, wherein a driver distal end includes a portion extractably engagable with the lead distal end portion.

5. The lead assembly as recited in claim 1, wherein a driver proximal end includes a pin portion couplable with a rotation facilitating tool.

6. The lead assembly as recited in claim 3, wherein the active fixation mechanism proximal end includes a fixation actuator detachably matable with the driver distal end.

7. The lead assembly as recited in claim 6, wherein the driver distal end includes a male end portion and the fixation actuator proximal end includes a female end portion.

8. A lead assembly, comprising:
   a lead body extending from a lead proximal end portion to a lead distal end portion, the lead body including two or more co-radial conductors disposed therein;
   an extendable and retractable active fixation mechanism disposed at the lead distal end portion;
   a lead lumen extending within the lead body from the lead proximal end portion to at least near an active fixation mechanism proximal end, the lumen at least partially formed within the outer diameter of the two or more co-radial conductors; and
   a driver removably and rotatably seatable within the lead lumen, the driver including a stylet or guidewire receiving lumen therein and a driver distal end having a portion detachably matable with the active fixation mechanism proximal end;
   wherein the driver is capable of being removed from the lead assembly after detachably mating with the active fixation mechanism.

9. The lead assembly as recited in claim 8, wherein the active fixation mechanism is actuatable by rotation of the driver.

10. The lead assembly as recited in claim 8, wherein the lead lumen is formed, at least in part, by the two or more co-radial conductors.

11. The lead assembly as recited in claim 8, wherein a driver proximal end includes a portion couplable with a rotation facilitating tool.

12. The lead assembly as recited in claim 8, wherein a driver distal end includes a portion extractably engagable with the lead distal end portion.

13. The lead assembly as recited in claim 8, wherein an outer diameter of the lead body is about 5.5 Fr or less.

14. The lead assembly as recited in claim 8, wherein the driver distal end includes a flat-head portion, a Phillips-head portion, or a hexagonal configuration portion.

15. A driver comprising a driver body removably and rotatably seatable within a lead lumen, the driver body extending from a driver proximal end to a driver distal end having a stylet or guidewire receiving lumen disposed therein; the distal end including a portion detachably matable with an extendable and retractable active fixation mechanism; and the driver proximal end including a portion couplable with a rotation facilitating tool; wherein the driver is removable from the lead after detachably mating with the active fixation mechanism.

16. The driver as recited in claim 15, wherein the driver distal end includes a portion extractably engagable with the active fixation mechanism.

17. The driver as recited in claim 15, wherein the driver body is composed, at least in part, of one or a combination of polyethylene terephthalate, polyimide, polyethylene tetrafluoroethylene, polytetrafluoroethylene, or polyurethane.

18. The driver as recited in claim 15, wherein the driver body is composed, at least in part, of a coiled wire or a braided metal wire.

* * * * *